(12) United States Patent
O'Neil et al.

(10) Patent No.: US 9,364,491 B2
(45) Date of Patent: *Jun. 14, 2016

(54) ANTIMICROBIAL COMPOSITIONS WITH CYSTEAMINE

(71) Applicant: Novabiotics Limited, Craibstone (GB)

(72) Inventors: Deborah O'Neil, Craibstone (GB); Cedric Charrier, Craibstone (GB)

(73) Assignee: NOVABIOTICS LIMITED, Aberdeen (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/460,953

(22) Filed: Aug. 15, 2014

(65) Prior Publication Data

US 2014/0357592 A1 Dec. 4, 2014

Related U.S. Application Data

(60) Division of application No. 13/486,778, filed on Jun. 1, 2012, which is a continuation-in-part of application No. PCT/GB2011/001721, filed on Dec. 14, 2011.

(60) Provisional application No. 61/423,000, filed on Dec. 14, 2010.

(30) Foreign Application Priority Data

Dec. 14, 2010 (GB) .................................. 1021186.0

(51) Int. Cl.
  *A61K 31/7036* (2006.01)
  *A61K 31/145* (2006.01)
  *A61K 31/496* (2006.01)

(52) U.S. Cl.
  CPC ........... *A61K 31/7036* (2013.01); *A61K 31/145* (2013.01); *A61K 31/496* (2013.01)

(58) Field of Classification Search
  CPC .............. A61K 31/145; A61K 31/496; A61K 31/7036; A61K 2300/00
  See application file for complete search history.

(56) References Cited

U.S. PATENT DOCUMENTS

| | | | |
|---|---|---|---|
| 5,902,283 A | 5/1999 | Darouiche | |
| 6,461,607 B1 | 10/2002 | Farmer | |
| 2009/0258030 A1 | 10/2009 | Chi et al. | |
| 2010/0255092 A1 | 10/2010 | Ravishankar et al. | |

FOREIGN PATENT DOCUMENTS

| | | |
|---|---|---|
| WO | WO 2007/050565 A2 | 3/2007 |
| WO | WO 2008143705 A2 | 11/2008 |
| WO | WO 2009/086942 A1 | 7/2009 |
| WO | WO 2010/112848 A2 | 7/2010 |

OTHER PUBLICATIONS

Anthony, T.U., et al., "Stability of Antibiotics Used for Antibiotic-Lock Treatment of Infections of Implantable Venous Devices (Ports)," Antimicrobial Agents and Chemotherapy, v. 43, n. 8, p. 2074-2076, Aug. 1999.

*Primary Examiner* — Michael G Hartley
*Assistant Examiner* — Robert Cabral
(74) *Attorney, Agent, or Firm* — Morgan, Lewis & Bockius LLP

(57) ABSTRACT

The invention relates to products comprising an antibiotic agent and a second agent being a dispersant or an anti-adhesive agent, in particular a mucolytic dispersant or a mucolytic anti-adhesive agent, which are useful in relation to the prevention and treatment of bacterial infections.

9 Claims, 9 Drawing Sheets

| PA01 - MIC (µg/ml) | Normal | | Mucin | | NaCl | |
|---|---|---|---|---|---|---|
| | Alone | + NM001 (250µg/ml) | Alone | + NM001 (250µg/ml) | Alone | + NM001 (250µg/ml) |
| Tobramycin | 1 | 0.25 | 8 | 1 | 4 | 0.5 |

FIG. 4 Antibiofilm Activity of Cysteamine Alone and in Combination with Tobramycin against Established *P. aeruginosa* PAO1 Biofilm
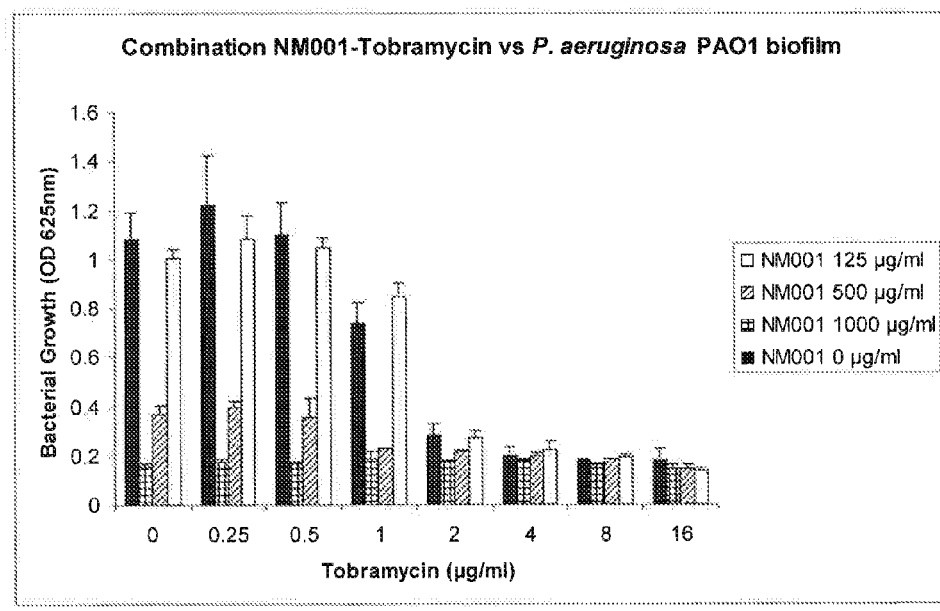
FIG. 5 Post-Antimicrobial Effect of Cysteamine (NM001) in Combination with Tobramycin (TOB) versus *P. aeruginosa* PAO1 biofilms
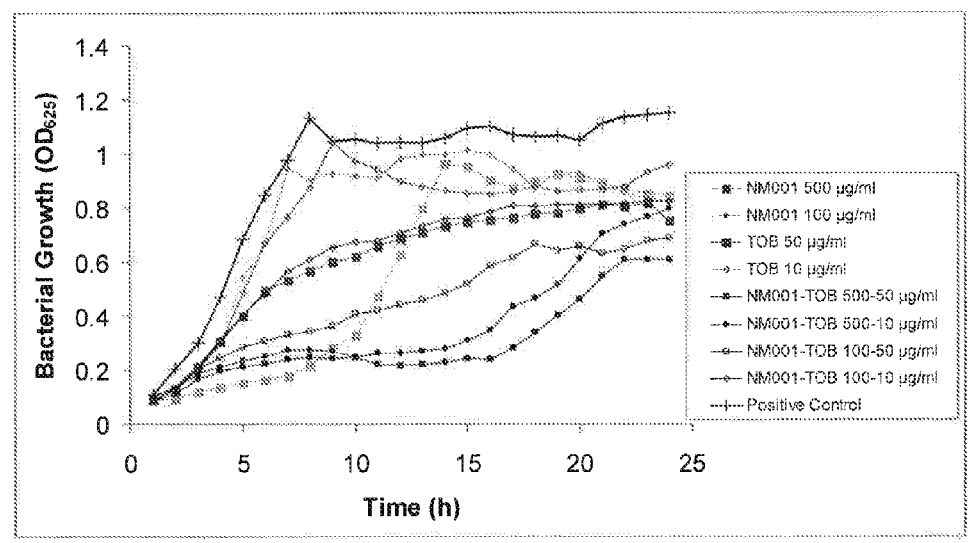

FIG. 6 Cysteamine (NM001) Enhances the Antimicrobial Activity of Tobramycin Against the Multidrug-Resistant *Burkholderia cepacia* NCTC10743
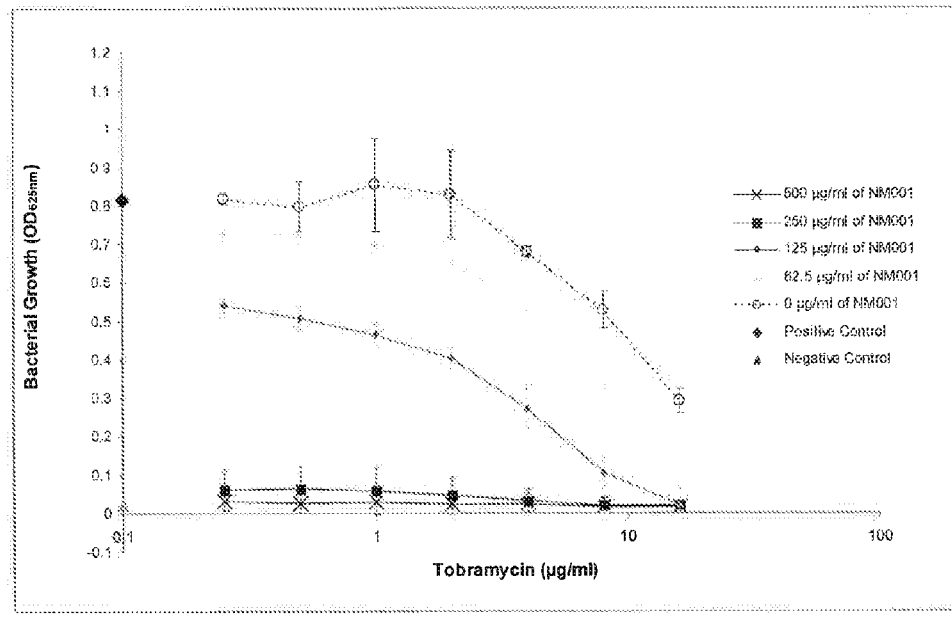
FIG. 7
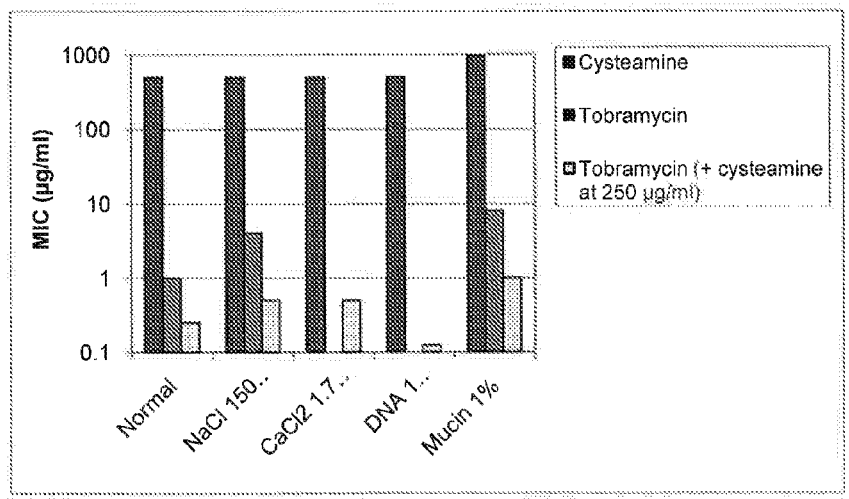

FIG. 8 Mucolytic Activity of Cysteamine versus Other Disulphide Bond Disrupters and Mucolytic Agents
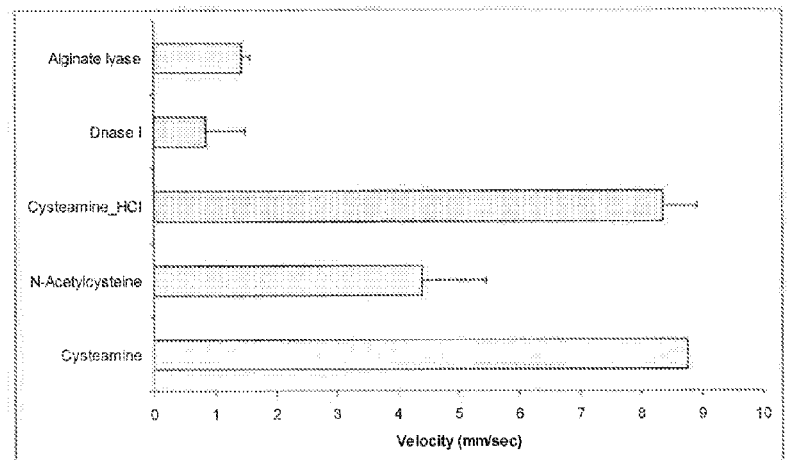
FIG. 9 Post-Antimicrobial Effect of Cysteamine (NM001) in Combination with Tobramycin versus *P. aeruginosa* PAO1 biofilms
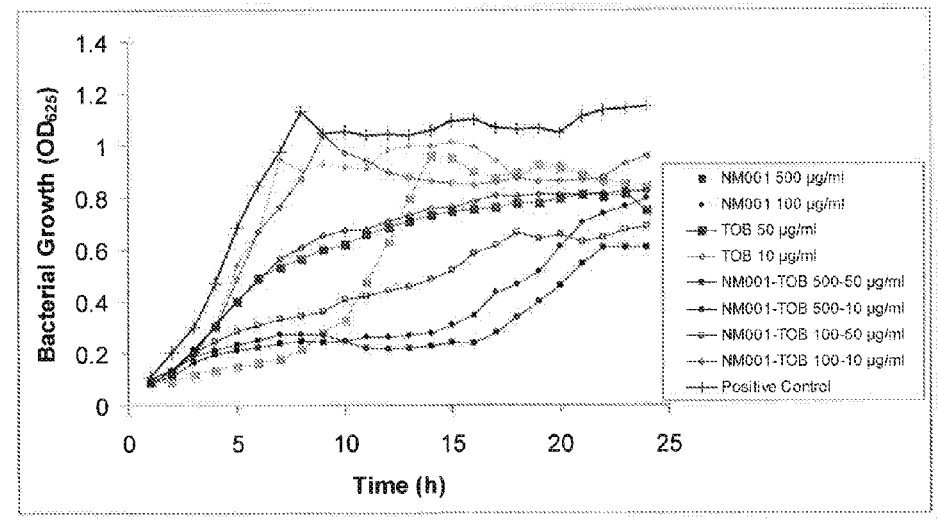

ANTIMICROBIAL COMPOSITIONS WITH CYSTEAMINE

CROSS-REFERENCE TO RELATED APPLICATIONS

The present application is a divisional application of U.S. application Ser. No. 13/486,778 filed Jun. 1, 2012, which is a continuation-in-part of PCT application no. PCT/GB2011/001721 filed Dec. 14, 2011, which claims the benefit of GB application no. 1021186.0 filed on Dec. 14, 2010 and U.S. provisional application No. 61/423,000 filed on Dec. 14, 2010, each of which is incorporated herein by reference in its entirety for all purposes.

FIELD OF THE INVENTION

The invention relates to products, compositions, methods and uses which are useful in relation to the prevention and treatment of bacterial infections.

BACKGROUND OF THE INVENTION

Antibiotics are widely used, both in human/veterinary medicine and also agriculture, and this has lead to an increasing problem of drug resistance to currently available antibiotics. This is particularly relevant to infectious conditions or diseases that are treated with single antibiotics (otherwise known as monotherapy). As such, there is a significant need not just for effective and safe new treatments but those that have a mode of action that minimises or negates the risk of eventual development of drug resistance in target pathogen populations and for therapies that can be used in combination with other treatments in order to minimise the opportunity for resistance and extending the utility of currently available antimicrobials.

Bacterial infections of mucous-rich environments such as the lung are common in diseases such as cystic fibrosis (CF). However, conventional antibiotics do not tend to work well in such environments and their antibacterial effectiveness is greatly diminished when used in such environments.

A microbial biofilm is a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature, are commonly found in a wide range of environments. Biofilms are being increasingly recognised by the scientific and medical community as being implicated in many infections, and especially their contribution to the recalcitrance of infection treatment.

Biofilms are etiologic agents for a number of disease states in mammals and are involved in 80% of infections in humans. Examples include skin and wound infections, middle-ear infections, gastrointestinal tract infections, peritoneal membrane infections, urogenital tract infections, oral soft tissue infections, formation of dental plaque, eye infections (including contact lens contamination), endocarditis, infections in cystic fibrosis, and infections of indwelling medical devices such as joint prostheses, dental implants, catheters and cardiac implants.

Planktonic microbes (i.e., microorganisms suspended or growing in a liquid medium) are typically used as models for antimicrobial susceptibility research as described by the Clinical and Laboratory Standards Institute (CLSI) and European Committee on Antimicrobial Susceptibility Testing (EUCAST). Microbes in biofilms are significantly more resistant to antimicrobial treatment than their planktonic counterparts. However, there is no standardized method for the study of antibiotic susceptibility of biofilm microbes.

Biofilm formation is not limited solely to the ability of microbes to attach to a surface. Microbes growing in a biofilm are able to interact more between each other than with the actual physical substratum on which the biofilm initially developed. For example, this phenomenon favours conjugative gene transfer, which occurs at a greater rate between cells in biofilms than between planktonic cells. This represents an increased opportunity for horizontal gene transfer between bacteria, and is important because this can facilitate the transfer of antibiotic resistance or virulence determinant genes from resistant to susceptible microbes. Bacteria can communicate with one another by a system known as quorum sensing, through which signalling molecules are released into the environment and their concentration can be detected by the surrounding microbes. Quorum sensing enables bacteria to co-ordinate their behaviour, thus enhancing their ability to survive. Responses to quorum sensing include adaptation to availability of nutrients, defense against other microorganisms which may compete for the same nutrients and the avoidance of toxic compounds potentially dangerous for the bacteria. It is very important for pathogenic bacteria during infection of a host (e.g. humans, other animals or plants) to co-ordinate their virulence in order to escape the immune response of the host in order to be able to establish a successful infection.

Biofilm formation plays a key role in many infectious diseases, such as cystic fibrosis and periodontitis, in bloodstream and urinary tract infections and as a consequence of the presence of indwelling medical devices. The suggested mechanisms by which biofilm-associated microorganisms elicit diseases in their host include the following: (i) delayed penetration of the antimicrobial agent through the biofilm matrix, (ii) detachment of cells or cell aggregates from indwelling medical device biofilms, (iii) production of endotoxins, (iv) resistance to the host immune system, (v) provision of a niche for the generation of resistant organisms through horizontal gene transfer of antimicrobial resistance &/or virulence determinant genes, and (vi) altered growth rate (i.e. metabolic dormancy) (Donlan and Costerton, Clin Microbiol Rev 15: 167-193, 2002; Parsek and Singh, Annu Rev Microbiol 57: 677-701, 2003; Costerton J W, Resistance of biofilms to stress. In 'The biofilm primer'. (Springer Berlin Heidelberg). pp. 56-64.2007).

Recent experimental evidence has indicated the existence within biofilms of a small sub-population of specialized non-metabolising persister cells (dormant cells). It is thought that these cells may be responsible for the high resistance/tolerance of biofilm to antimicrobial agents. Multi-drug-tolerant persister cells are present in both planktonic and biofilm populations and it appears that yeasts and bacteria have evolved analogous strategies that assign the function of survival to this sub-population. The protection offered by the polymeric matrix allows persister cells to evade elimination and serve as a source for re-population. There is evidence that persisters may be largely responsible for the multi-drug tolerance of microbial biofilms (LaFleur et al., Antimicrob Agents Chemother. 50: 3839-46, 2006; Lewis, Nature Reviews Microbiology 5, 48-56 2007).

There remains a need for better therapies for treating and preventing bacterial infections, in particular those associated with mucolytic environments such as the CF lung. In addition there remains a need to limit the amount or doses of antibiotics used with the introduction of novel, replacement therapies or adjunt treatments that can improve the effectiveness of currently available treatments in the treatment or prevention of bacterial infections, in particular in a biofilm setting.

SUMMARY OF THE INVENTION

According to a first aspect of the present invention there is provided a product comprising an antibiotic agent and a second agent being a dispersant or an anti-adhesive agent, in particular a mucolytic dispersant or a mucolytic anti-adhesive agent.

According to one embodiment, the second agent may have antimicrobial activity. Alternatively, the second agent may not have inherent direct antimicrobial activity.

The invention includes pharmaceutical products comprising at least one antibiotic agent and at least one dispersant or at least one anti-adhesive agent, in particular a mucolytic dispersant or a mucolytic anti-adhesive agent.

There is also provided the product described above for therapeutic use.

According to a further aspect of the present invention there is provided the product for use in the treatment or prevention of a bacterial infection.

The bacterial infection may be a disseminated planktonic bacterial infection or in particular, a bacterial biofilm.

There is also provided a method of preventing or treating a bacterial infection comprising the steps of administering a therapeutically effective amount of the product of the invention to a patient in need thereof. The antibiotic agent and the dispersant or anti-adhesive agent may be administered in a combined or sequential manner.

BRIEF DESCRIPTION OF THE DRAWINGS

The invention will now be described by way of Examples only with reference to the following Figures in which:

FIG. 4: shows a histogram comparing antibiofilm activity of cysteamine alone and in combination with Tobramycin against established *P. aeruginosa* PAO1 biofilm: a dose response study allowed the identification of the minimum biofilm eradication concentration (MBEC) of cysteamine against established *P. aeruginosa* PAO1 biofilms and the quantification of the additive activity with Tobramycin. The MBEC of cysteamine alone was 1000 µg/ml and Tobramycin showed an MBEC of 4 µg/ml. When combined, however, total biofilm eradication was obtained with 500 µg/ml cysteamine and 1 µg/ml Tobramycin. Therefore, the fractional inhibitory concentration (FIC) of such a combination is 0.75, which indicates additivity between the two antimicrobial agents. Therefore, the mucolytic/antimicrobial agent cysteamine has the potential to enhance the antibiofilm activity of conventional antibiotics, which may have implications in lowering the spread of antimicrobial resistance and costs of treatment.

FIG. 5: shows a graph post-antimicrobial effect of cysteamine (NM001) in combination with Tobramycin (TOB) versus *P. aeruginosa* PAO1 biofilms.

FIG. 6: shows a graph demonstrating that cysteamine (NM001) enhances the antimicrobial activity of Tobramycin against the multidrug-resistant *Burkholderia cepacia* NCTC10743. The additive antimicrobial activity of cysteamine and Tobramycin was also identified against the multidrug-resistant strain *Burkholderia cepacia* NCTC10743. The $MIC_{100}$ of Tobramycin was higher than 16 µg/ml while cysteamine showed $MIC_{100}$ at 500 µg/ml. When combined together, cysteamine was able to enhance the activity of Tobramycin and its $MIC_{100}$ was 0.25 µg/ml in combination with 250 µg/ml cysteamine. This leads to a FIC index of less than 0.51, which indicates at least additive antimicrobial activity and possibly synergy between these two compounds.

FIG. 7: shows a histogram demonstrating the antimicrobial activity of Tobramycin and cysteamine against *P. aeruginosa* PAO1 planktonic cells alone and in combination in physiologically-relevant concentrations as found in the lungs of cystic fibrosis (CF) patients. The antimicrobial activity ($MIC_{100}$) of cysteamine was compared in normal condition (as described in the CLSI M7-A7 method—see Appendix 1) and in the presence of 150 mM sodium chloride (NaCl), 1.7 mM calcium chloride ($CaCl_2$), 1 mg/ml DNA or 1% (w/v) porcine gastric mucin in triplicate, in 96 well plates. Bacterial growth was followed over a 24 h period and absorbance read using a BioTek microtitre plate reader at 625 nm. Total bacterial growth inhibition was retained in the presence of NaCl, $CaCl_2$ or DNA and at two-fold the normal $MIC_{100}$ in the presence of mucin. Tobramycin activity was inhibited in the presence of the divalent cation $ca^{2+}$ and in the presence of the anionic polymer DNA. When combined with cysteamine, Tobramycin activity was retained in all conditions tested at concentrations up to 4-fold higher its normal MIC.

FIG. 8: is a histogram showing the mucolytic activity of cysteamine versus other disulphide bond disrupters and mucolytic agents. The mucolytic activity of cysteamine was compared to other mucolytic agents such as N-acetylcysteine (Mucomyst®), DNase I (Dornase Alfa®), alginate lyase and cysteamine hydrochloride by measuring the viscosity of a mucin solution following treatment. The mucin of porcine stomach (Sigma-Aldrich, Gillingham, UK) was prepared in sterile purified water at 20% (w/v). The mucolytic agents were prepared at 10 mg/ml in 20% (w/v) mucin solution. The velocity of the mucin was measured following approximately 5 minutes exposure to the mucolytic agents. The data shows the average and standard deviation values of independent duplicate experiments.

FIG. 9: is a graph showing the post-antimicrobial effect of cysteamine (NM001) in combination with Tobramycin versus *P. aeruginosa* PAO1 biofilms. This shows the antibiofilm activity of cysteamine in combination with Tobramycin at two different concentrations, while the post-antimicrobial effect (PAE) of these compounds was also determined by following bacterial growth following treatment of the biofilms

DETAILED DESCRIPTION OF THE INVENTION

Product

Figures 1A, 1B:
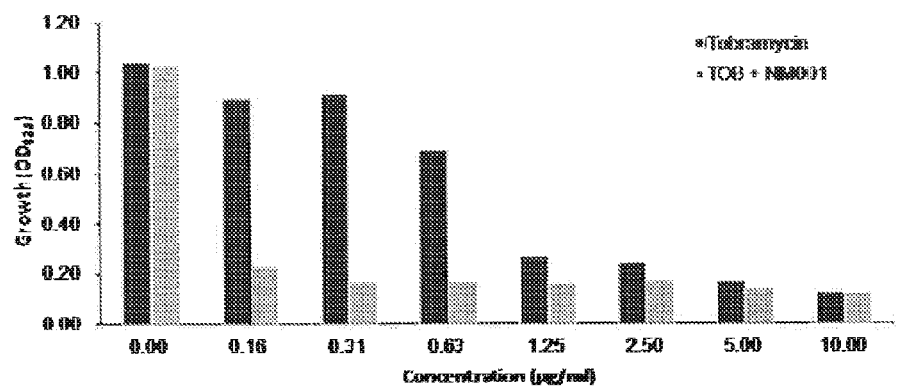
FIGS. 1a and 1b: provide a comparison of the antibacterial activity of Tobramycin and cysteamine (NM001) against *Pseudomonas* planktonic cells when administered separately, and in combined form. NM001 reduces the MIC of Tobramycin against planktonic cells by at least 4-fold (FIG. 1b)
Figures 2, 3:
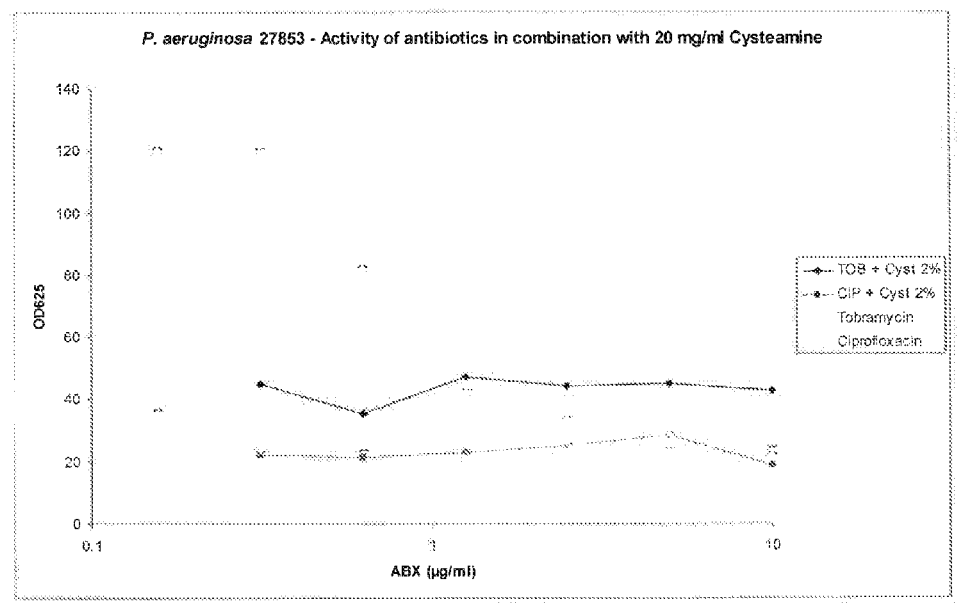
FIG. 2: provides a comparison of the antibacterial activity of Tobramycin and Ciprofloxacin against *Pseudomonas aeruginosa* cells cultured in a mucous environment replicating that found within the CF lung when administered alone and in combination with cysteamine.
FIG. 3: provides a comparison of the activity of Tobramycin alone and when in combination with cysteamine (NM001) against *Pseudomonas aeruginosa* cells cultured in a non-mucous environment and when cultured in a mucous environment replicating that found within the CF lung (in the presence of NaCl and/or mucin). NM001 restores antibiotic activity to conventional antibiotics in a mucous environment.
Figure 10:
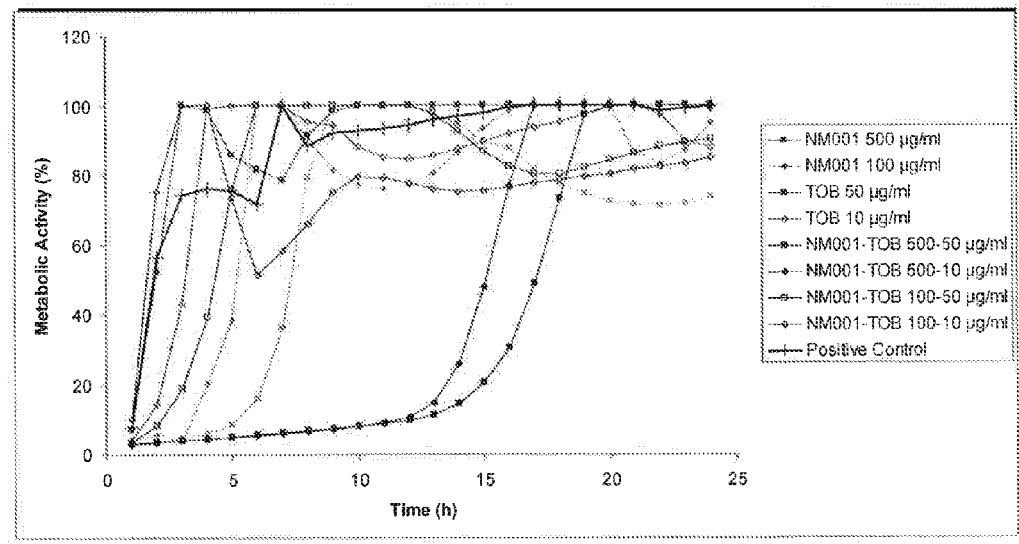
FIG. 10: shows a graph demonstrating the inhibition of microbial metabolic activity of the *P. aeruginosa* PAO1 biofilms following treatment with cysteamine (NM001) in combination with Tobramycin. This shows the metabolic activity of the biofilms following treatment. The data demonstrate the antibiofilm activity of cysteamine, alone and in combination with Tobramycin, with a significant PAE as demonstrated by the delayed bacterial growth and reduced metabolic activity of the biofilm.

According to a first aspect of the present invention there is provided a product comprising an antibiotic agent and a second agent being a dispersant or an anti-adhesive agent.

According to one embodiment, the antibiotic is a non-peptide antibiotic. Preferably, the product of the present invention does not contain any peptides.

The products of the present invention are effective in the treatment and prevention of bacterial infections, including bacterial infections of a mucous environment. Such conditions are commonly very difficult to treat as conventional antibiotics are less effective in such environments. In addition, the agents of the product of the present invention generally combine synergistically to provide surprisingly high antibacterial activity. The amount of antibiotic required is thus minimised. Alternatively, the agents of the product of the present invention may combine additively.

The products have the advantage that they demonstrate antibacterial activity against established bacterial colonies, including the persister cells present in bacterial colonies, such as bacterial biofilms, which is an essential step towards the eradication of biofilms.

Synergistic Effect

Surprisingly, it has been found that the antibacterial action of the antibiotic agent and the dispersant or anti-adhesive agent generally increase synergistically upon combination.

The Fractional Inhibitory Concentration (FIC) corresponds to an interaction coefficient indicating whether the combination of antimicrobial agents is synergistic, additive, antagonist or neutral. The FIC is determined by comparing the activity of an agent in combination (MIC of agent A+agent B) with the activity of the agent alone (MIC of agent A or agent B) as follow (Singh et al., 2000):

$$FIC = MIC_{A[combination]}/MIC_{A[alone]} + MIC_{B[combination]}/MIC_{B[alone]}$$

Additive combinations of two antimicrobial agents are indicated by a FIC index of 1, whereas a FIC index <1 indicates synergistic combinations. Neutral combinations would give a FIC between 1 and 4, a FIC index higher than 4 indicates antagonist effects between the two antimicrobial agents.

Generally the FIC index of the combination of the components of the product of the present invention is less than 1, typically less than 0.9, suitably less than 0.8, advantageously less than or around 0.75, for example less than or around 0.5. Alternatively, the FIC index of the combination of the components of the product of the present invention may be more than 1; generally between 1 and 2; typically between 1 and 1.5, suitably between 1 and 1.2.

In mucolytic environments conventional antibiotics such as Tobramycin, Colistin, Gentamicin or Ciprofloxacin do not exhibit the same level of antibacterial activity as when they are in non-mucolytic environments. Surprisingly, the antibacterial activity of such conventional antibiotics is increased upon administration of a dispersant or anti-adhesive agent such as cysteamine. The antibiotics and anti-adherent or dispersant act synergistically and when administered together or sequentially the antibacterial activity of the active agents is far higher than when administered separately.

Generally, the antibacterial activity of the product of the present invention is at least two times greater than the antibacterial activity of antibiotic agent alone, typically the antibacterial activity of the product of the present invention is at least four times higher than the antibiotic agent alone, suitably at least an eight times higher, generally at least, or around ten times higher.

Generally the minimal inhibitory concentration (MIC) of the product of the present invention is at least two times lower than the MIC of the antibiotic agent alone in connection with the same bacterial pathogen, suitably at least four times lower, typically at least eight time lower, advantageously at least or around ten times lower.

To obtain synergistic effect the agents of the product of the present invention may be administered together or sequentially, preferably no more than 10 minutes apart.

Surprisingly, the antibiotic resistance/insensitivity of a bacterial strain may be overcome by administering the antibiotic together or sequentially with a dispersant or anti-adhesive agent such as cysteamine or N-acetylcysteine. In particular, the antibiotic activity of antibiotics against an antibiotic resistant/insensitive bacteria strain may be reversed.

Antibiotic Agent

The term "antibiotic" is used to refer to antibacterial agents that may be derived from bacterial sources. Antibiotic agents may be bactericidal and/or bacteriostatic.

Generally the antibiotic agent is of the group consisting of aminoglycosides, ansamycins, carbacephem, carbapenems, cephalosporins (including first, second, third, fourth and fifth generation cephalosporins), lincosamides, macrolides, monobactams, nitrofurans, quinolones, penicillin, sulfonamides, polypeptides and tetracyclines. Alternatively or additionally the antibiotic agent may be effective against mycobacteria.

According to one embodiment, the antibiotic agent may be an aminoglycoside such as Amikacin, Gentamicin, Kanamycin, Neomycin, Netilmicin, Tobramycin or Paromomycin.

According to one embodiment, the antibiotic agent may be an http://en.wikipedia.org/wiki/Ansamycin such as Geldanamycin and Herbimycin Alternatively the antibiotic agent may be a carbacephem such as Loracarbef.

According to a further embodiment, the antibiotic agent is a carbapenem such as Ertapenem, Doripenem, Imipenem/Cilastatin or Meropenem.

Alternatively the antibiotic agent may be a cephalosporins (first generation) such as Cefadroxil, Cefazolin, Cefalexin, Cefalotin or Cefalothin, or alternatively a Cephalosporins (second generation) such as Cefaclor, Cefamandole, Cefoxitin, Cefprozil or Cefuroxime. Alternatively the antibiotic agent may be a Cephalosporins (third generation) such as Cefixime, Cefdinir, Cefditoren, Cefoperazone, Cefotaxime, Cefpodoxime, Ceftibuten, Ceftizoxime and Ceftriaxone or a Cephalosporins (fourth generation) such as Cefepime and Ceftobiprole.

The antibiotic agent may be a lincosamides such as Clindamycin and Azithromycin, or a macrolide such as Azithromycin, Clarithromycin, Dirithromycin, Erythromycin, Roxithromycin, Troleandomycin, Telithromycin and Spectinomycin.

Alternatively the antibiotic agent may be a monobactams such as Aztreonam, or a nitrofuran such as Furazolidone or Nitrofurantoin.

The antibiotic agent may be a penicillin such as Amoxicillin, Ampicillin, Azlocillin, Carbenicillin, Cloxacillin, Dicloxacillin, Flucloxacillin, Mezlocillin, Nafcillin, Oxacillin, Penicillin G or V, Piperacillin, Temocillin and Ticarcillin.

The antibiotic agent may be a sulfonamide such as Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, and Trimethoprim-Sulfamethoxazole (Co-trimoxazole) (TMP-SMX).

The antibiotic agent may be a quinolone such as Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin.

According to one embodiment, the antibiotic agent may be a polypeptide such as Bacitracin, Colistin and Polymyxin B.

Alternatively, the antibiotic agent may be a tetracycline such as Demeclocycline, Doxycycline, Minocycline and Oxytetracycline Alternatively or additionally the antibiotic agent may be effective against mycobacteria.

In particular the antibiotic agent may be Clofazimine, Lamprene, Dapsone, Capreomycin, Cycloserine, Ethambutol, Ethionamide, Isoniazid, Pyrazinamide, Rifampicin, Rifabutin, Rifapentine or Streptomycin.

Generally the antibiotic agent is active in the treatment or prophylaxis of infections caused by gram-negative or gram-positive bacteria, such as *Escherichia coli* and *Klebsiella* particularly *Pseudomonas aeruginosa*.

The Second Agent

The second agent may be selected from a dispersant and an anti-adhesive agent. In particular, the second agent is selected from a mucolytic dispersant and a mucolytic anti-adhesive agent. The second agent may be any agent which inhibits the formation of a bacterial colony, in particular any agent which inhibits biofilm formation. By way of example, the second agent may inhibit bacterial adhesion, hydrophobicity or slime production.

According to one embodiment of the present invention the second agent is not a peptide.

The term "dispersant" is intended to include any agent capable of dispersing bacterial particles, thus inhibiting the formation of a bacterial colony. In particular, the dispersant may disperse the particles of a bacterial biofilm. The dispersant may promote the dispersion of slime produced by bacterial microbes, mucous which forms part of the biofilm for example mucous produced by the cells to which the biofilm microbes adheres, and biofilm bacteria.

The dispersant may be a mucolytic agent. The mucolytic agent may be an enzyme for example a DNase, alginase, protease or carobohydrase. Alternatively the mucolytic agent may be a small molecule for example an amine such as an aminothiol or an acid such as ethylenediaminetetraacetic acid (EDTA). The amine may be selected from acetylcysteine and cysteamine, preferably cysteamine.

The term "anti-adhesive agent" is intended to include any agent capable of inhibiting adhesion between cells, proteins and organisms e.g. microbes thereby preventing the formation of a bacterial colony, in particular bacterial biofilm formation or promoting biofilm self-destruction. In particular, the anti-adhesive agent may prevent the adhesion to a surface or substrate of all cell types encountered in microbial biofilms in particular free living microbes i.e. planktonic cells. Anti-adhesive agents may include, but are not limited to, hyaluronan, heparin or Carbopol 934.

The second antibiofilm agent may be an antibacterial agent. The antibacterial agent may be a mucolytic agent for example a mucolytic agent having both mucolytic and antibacterial activity. Preferably the antibacterial agent is cysteamine Pharmaceutical Product The above mentioned active agents may be administered as free or fixed combinations. Free combinations may be provided as combination packages containing all the active agents in free combinations. Fixed combinations are often tablets or capsules.

The agents of the invention may be administered in the form of pharmaceutically acceptable salts. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The invention thus includes pharmaceutically-acceptable salts of the disclosed compounds wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The Products of the Invention

According to one embodiment, the antibiotic agent of the product of the present invention does not comprise peptides. Suitably, the product of the present invention does not comprise peptides.

A preferred product comprises a non-peptide antibiotic and a dispersant, in particular a mucolytic dispersant such as cysteamine.

The ratio of the antibiotic agent to the second agent in the products of the invention may be from 1:10 to 10:1; generally at least 2:1 for example at least 3:1 or 4:1. Alternatively, the ratio of the antibiotic agent to the second agent in the products of the invention may be from 1:100 1:2000, for example from 1:500 to 1:1000. According to one embodiment, the ratio of the antibiotic agent to the second agent is approximately 1:1. Preferably the first antibiotic agent is a non-peptide antibiotic and the second agent is cysteamine and the product contains these components at a ratio from 2:1 up to 4:1. According to a further embodiment the ratio may be approximately 1:1.

The active agents may be administered simultaneously, sequentially or separately. The active agents may be provided as a combination package. The combination package may contain the product of the invention together with instructions for simultaneous, separate or sequential administration of each of the active agents. For sequential administration, the active agents can be administered in any order.

The active agents of the product of the invention may be provided as pharmaceutical compositions additionally containing one or more pharmaceutically acceptable diluents, excipients and/or carriers. This applies to both fixed and free combinations.

The active agents of the present invention may be administered by any suitable route known to those skilled in the art, preferably in the form of a pharmaceutical composition adapted to such a route, and in a dose effective for the treatment intended. The active compounds and composition may, for example, be administered parenterally, orally, intranasal, intrabronchial, enterally, transdermally, sublingually, rectally, vaginally, ocularly, or topically. Both local and systemic administration is contemplated.

For the purposes of parenteral administration ("parenteral" as used herein, refers to modes of administration which include intravenous, intramuscular, enteral, intraperitoneal, intrasternal, subcutaneous and intraarticular injection and infusion of which intravenous (including continuous intravenous administration) is most preferred) solutions in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

The products of the invention can also be administered intranasally or by inhalation and are conveniently delivered in the form of a dry powder inhaler or an aerosol spray presentation from a pressurised container, pump, spray, atomiser, nebuliser, with or without the use of a suitable propellant.

Alternatively the products of the invention can be administered in the form of a suppository or pessary, or they may be applied topically in the form of a gel, hydrogel, lotion, solution, cream, ointment or powder. The products of the invention may be dermally or transdermally administered, for example, by use of a skin patch, depot or subcutaneous injection. They may also be administered by pulmonary or rectal routes.

For oral administration, the pharmaceutical composition may be in the form of; for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose; mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable carrier.

The products of the invention may also find application as/in an oral formulation wherein the product is formulated in a carrier, for example selected from films, tapes, gels, microspheres, lozenges, chewing gum, dentrifices and mouthwash.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

The products of the invention are preferably administered to the respiratory tract. Thus, the present invention also provides aerosol pharmaceutical formulations comprising a product of the invention. Also provided is a nebuliser or inhaler containing a product of the invention.

Additionally, the products of the invention may be suited to formulation as sustained release dosage forms and the like. The formulations can be so constituted that they release the active agents, for example, in a particular part of the intestinal or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

The products of the invention may include synergistically effective amounts of each active agent defined herein. The invention therefore includes products comprising a synergistically effective amount of (i) an antibiotic agent (which may be a non-peptide antibiotic agent) (ii) a second agent which is typically cysteamine. The product may be for use in the manufacture of a medicament, for simultaneous, separate or sequential administration said agents in the treatment of a microbial infection for example a bacterial infection. "Synergistically", as used herein, may describe the action of the two or more agents of the product of the invention working together to produce an effect greater than the expected combined effect of the agents used separately.

In a further aspect of the invention there is provided a substrate to which a product of the invention is applied or attached. Preferably, the substrate is suitable for application to wounds or delivery to wound sites. Preferably, the substrate allows for the transfer of the active agents of the product of the invention from the substrate to a wound bed to achieve their antibacterial effect. The substrate may be a dressing, for example, wound dressing. The dressing may comprise a fabric material or it may be a collagen-like material. The substrate may be in any suitable form for application to a wound, typically the substrate may be in the form of a hydrogel, colloid, ointment, cream, gel, foam or spray.

The products of the invention may also find application as/in a disinfectant or biocide. In this context, the pharmaceutical compositions of the invention may be applied, either alone or in combination with other disinfecting agents, to a surface to be treated. As used herein a "surface to be treated" may be a substrate as defined herein and may include medical devices and indwelling devices, e.g. stents, catheters, peritoneal dialysis tubing, draining devices, joint prostheses, dental implants and the like.

Methods and Use

The invention provides a method of treating or preventing a bacterial infection. The bacterial infection may typically be a disseminated infection or in particular in a mucous-rich environment, such as the lung, for example the lung of a patient suffering from CF or bacterially-associated chronic obstructive pulmonary disease (COPD). The method of the present invention comprises the step of administering to the environment a product according to the invention. The method may be in vivo or ex vivo.

In mucous-rich environments conventional antibiotics such as Tobramycin, Colistin, Gentamicin or Ciprofloxacin do not exhibit the same level of antibacterial activity as when they are in low mucous environments. Surprisingly, the antibacterial activity of antibiotics is increased upon administration of a dispersant or anti-adhesive agent such as cysteamine Advantageously the method comprises the step of administering An antibiotic agent; and A second agent being a dispersant or an anti-adhesive agent, preferably cysteamine.

Where the method of the present invention is used to treat bacterial infections associated with CF, the antibiotic agent is preferably Tobramycin, Colistin, Gentamicin or Ciprofloxacin.

The environment may comprise any bacterial infection, including an infection caused by more than one microorganism, for example bacteria and any one of fungi, yeast, viruses and protozoa.

The bacterium may be a Gram-positive or a Gram-negative bacterium. A bacterial pathogen may be derived from a bacterial species selected from the group consisting of: *Staphylococcus* spp., e.g. *Staphylococcus aureus, Staphylococcus epidermidis; Enterococcus* spp., e.g. *Enterococcus faecalis; Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptococcus pneumoniae; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum; Yersinia* spp., e.g. *Yersinia pestis; Treponema* spp.; *Burkholderia* spp.; e.g. *Burkholderia mallei* and *B. pseudomallei.*

In particular the bacterium may include *Pseudomonas* spp., for example *Pseudomonas aeruginosa; Staphylococcus* spp., for example *Staphylococcus aureus* and *Staphylococcus epidermidis; Haemophilus* spp., for example *Haemophilus influenza; Burkholderia* spp., for example *Burkholderia cepacia; Streptococcus* spp., *Propionibacterium* spp., for example *Propionibacterium* acnes. Preferably the bacterium is selected from *Pseudomonas* spp., for example *Pseudomonas aeruginosa* and *Staphylococcus* spp., for example *Staphylococcus aureus* and *Staphylococcus epidermidis.*

The method of the invention may be used to minimise and, preferably, prevent the formation of bacterial colonies, in particular bacterial biofilms in a variety of environments including, but not limited to, household, workplace, laboratory, industrial environment, aquatic environment (e.g. pipeline systems), medical devices including indwelling devices such as defined herein, dental devices or dental implants, animal body for example human body.

The method of the invention may thus be used in the mouth to prevent the formation of plaque or caries on a human tooth or dental implant for example a denture.

The method of the invention may be used to prevent or restrict the formation of a bacterial colony. The method of the present invention may be used to prevent or treat bacterial infections including topical infections, oral infections and systemic infections. Topical infections may include wounds, ulcers and lesions for example, cutaneous wounds such cuts or burns, and conditions associated therewith.

Oral infections may include gingivitis, periodontitis and mucositis.

Systemic infections may include cystic fibrosis, COPD and other conditions associated with mucosal infections, for example, gastrointestinal, urogenital or other respiratory infections.

Another aspect of the invention resides in methods of treating, preventing or delaying the progression of a bacterial infection in a mammal, especially a human, by administering a therapeutically effective amount of a product of the invention to the mammal.

By an "effective" amount or "therapeutically effective amount" is meant an amount of one or more active substances which, within the scope of sound medical judgment, is sufficient to provide a desired effect without excessive toxicity, irritation, allergic response, or other problem or complication, commensurate with a reasonable benefit/risk ratio.

Thus the product of the invention may be useful in the prevention of, delay of progression of, or treatment of a disease or condition selected from the group consisting of skin and wound infections, middle-ear infections, gastrointestinal tract infections, peritoneal membrane infections, urogenital tract infections, oral soft tissue infections, formation of dental plaque, eye infections (including contact lense contamination), endocarditis, infections in cystic fibrosis, and infections of indwelling medical devices such as described herein.

The invention also includes methods of treatment in which a product of the invention is administered to a mammal together with one or more other antibacterial agents for example an antibiotic. Generally the product of the invention, and any composition of the present invention does not comprise any peptides.

The active agents mentioned in this specification can exist in different forms, such as free acids, free bases, esters and other prodrugs, salts and tautomers, for example, and the invention includes all variant forms of the agents.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Generally the term "approximately" is intended to encompass a range of 10% or less of any numerical value to which it is applied.

Further aspects and embodiments of the invention are set forth in the following description and claims.

EXAMPLES

Example 1

Activity of Antimicrobial Agents Against Bacterial Colonies 1.1 Bacterial Strains

*Pseudomonas aeruginosa* ATCC27853 and *Burkholderia cepacia* NCTC10743 were used in this study. Additional strains of *Pseudomonas aeruginosa* were used as shown in Tables 1 and 2.

1.2 Preparation of Antimicrobial Compounds

The antimicrobial agents tested in this study were cysteamine (NM001), Tobramycin, Ciprofloxacin, Colistin and Gentamicin. The agents were obtained from Sigma-Aldrich (Gillingham, UK) and stock solutions were prepared at 20 mg/ml in 14-18 MΩ·cm pure water (Purite HP40 water purification system, Oxon, UK). Once dissolved, the preparations were filter-sterilized using 0.22 μm filters (Millipore, Watford, England) and stored at −20° C.

1.3 Preparation of the Bacterial Inoculum

The bacterial inoculum was established by the dilution method from actively-growing cultures in Mueller-Hinton (MH) broth, standardized with 0.5 McFarland turbidity standard as described in the CLSI method M26-A.

1.4 Determination of the Minimum Inhibitory Concentration (MIC)

Both the bacterial inoculum and the antimicrobial agents, including the compounds structurally related to cysteamine, were added simultaneously to the plates. The plates were incubated at 37° C. for 24 h and the optical density was read at 625 nm on a microtitre plate reader (BioTek Powerwave XS, Winooski, USA). The MIC was obtained as the lowest concentration of antimicrobial showing total inhibition of bacterial growth.

Antimicrobial Efficacy of Cysteamine Derivatives Versus *P. aeruginosa*

A number of compounds related in chemical structure to cysteamine were examined for antimicrobial activity; cystamine (dihydrochloride salt), taurine and 2,3-dimercaptosuccinic acid. Other compounds chemically related to cysteamine are known, but are toxic, and are therefore of no utility in a drug of this nature.

Cysteamine:

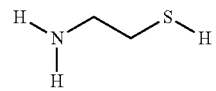

Cystamine:

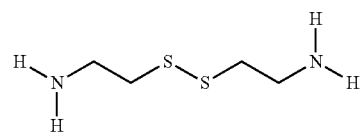

Taurine:

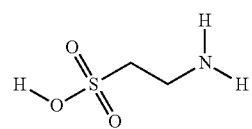

2,3-Dimercaptosuccinic Acid:

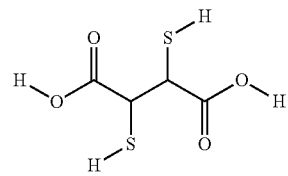

1.5 Determination of the MIC in Physiologically-Relevant Ionic Concentrations A similar method as described above (1.4) was used for the determination of the antimicrobial activity of cysteamine (Lynovex®) in the presence of high ionic concentrations. The antimicrobial activity ($MIC_{100}$) of cysteamine was compared in normal condition (as described in the CLSI M7-A7 method) and in the presence of 150 mM sodium chloride (NaCl), 1.7 mM calcium chloride ($CaCl_2$), 1 mg/ml DNA or 1% (w/v) porcine gastric mucin in triplicate, in 96 well plates. Bacterial growth was followed over a 24 h period and absorbance read using a BioTek microtitre plate reader at 625 nm.

1.6 Determination of Antibiofilm Activity

The antibiofilm activity was assessed using a microfluidic BioFlux 800 flow cell system (Fluxion, South San Francisco, USA). The microfluidic channels of a 48-well BioFlux plate were inoculated with a 0.5 McFarland equivalent inoculum of *P. aeruginosa* PAO1 in Mueller-Hinton broth. The microbial cells were allowed to attach and start forming microcolonies for approximately 30 min at 37° C. The mucolytic agents were prepared at 1 mg/ml in Mueller-Hinton broth and flowed through the microfluidic at a flow rate of 0.5 Dyn/cm2 (equivalent to 53 μl/h) for 16 h at 37° C. Microscopic observations were performed and pictures recorded using an inverted Axiovert 40 microscope at 100-fold magnification (Carl Zeiss, Welwyn Garden City, UK).

1.7 Determination of the Fractional Inhibitory Concentration (FIC)

The FIC corresponds to an interaction coefficient indicating whether the combination of antimicrobial agents is synergistic, additive, antagonist or neutral. The FIC is determined by comparing the activity of an agent in combination (MIC of agent A+agent B) with the activity of the agent alone (MIC of agent A or agent B) as follow (Singh et al., 2000):

$$FIC = MIC_{A[combination]}/MIC_{A[alone]} + MIC_{B[combination]}/MIC_{B[alone]}$$

Additive combinations of two antimicrobial agents are indicated by a FIC index of 1, whereas a FIC index <1 indicates synergistic combinations. Neutral combinations would give a FIC between 1 and 4, a FIC index higher than 4 indicates antagonist effects between the two antimicrobial agents.

The FIC was also calculated to assess the interaction of two antimicrobial agents in combination against bacterial samples.

1.8 Determination of the Post-Antimicrobial Effect (PAE) and Metabolic Activity The PAE was determined by transfer of 10 μl biofilm cultures into 90 μl sterile MH broth in triplicate in microtitre plates following treatment. Bacterial growth was followed on a BioTek plate reader for 24 h at 37° C. Microbial metabolic activity following treatment of the biofilms was determined using the same method as for PAE determination and adding 10% (v/v) of a fluorescent cell viability indicator, resazurin (Alamar Blue, Serotec), which detected microbial metabolic activity growth by increase in fluorescence. Fluorescence was measured over 24 h at 37° C. using a BioTek Synergy HT microplate reader (BioTek, Winooski, USA) at 530/590 nm.

1.9 Determination of the Mucolytic Activity

The mucolytic activity of cysteamine was compared to other mucolytic agents such as N-acetylcysteine (Mucomyst®), DNase I (Dornase Alfa®), alginate lyase and cysteamine hydrochloride by measuring the viscosity of a mucin solution following treatment. The mucin of porcine stomach (Sigma-Aldrich, Gillingham, UK) was prepared in sterile purified water at 20% (w/v). The mucolytic agents were prepared at 10 mg/ml in 20% (w/v) mucin solution. The velocity of the mucin was measured following approximately 5 minutes exposure to the mucolytic agents.

Results

2.1 Prevention and Treatment of Bacterial Colonisation

The range of concentrations of antimicrobial agents was 0-10 μg/ml.

2.1.1 Activity Against *P. aeruginosa* ATCC 27853

The MIC of Tobramycin and Ciprofloxacin was greatly reduced upon administration with cysteamine compared to administration alone. This effect was exhibited when in environments mimicking those found in a CF lung.

Determination of the FIC for this combination indicates that the antimicrobial agents have synergistic effects (FIC=0.75). The antimicrobial agents of the present invention act synergistically to provide an enhanced antibacterial effect. The antimicrobial effect of conventional antibiotics such as Tobramycin and Ciprofloxacin was maintained when they were administered in combination with cysteamine to a mucolytic environment.

2.2 Table 1: Fractional Inhibitory Concentration Index of Combinations of Cysteamine, Cysteamine Hydrochloride and N-Acetyl Cysteine and the Conventional Antibiotics Colistin, Ciprofloxacin, Tobramycin and Gentamicin Versus Selected Isolates of *Pseudomonas aeruginosa*

TABLE 1

| | | Cysteamine (NM001) | | | | | | | |
| | Antibiotic | NM001 FICI (Synergy) | | | | NM001 FICI (Additive) | | | |
| Strain | Resistance | Col | Cip | Tob | Gent | Col | Cip | Tob | Gent |
| Pa01 | Col$^R$ | 0.38 | N | 0.31 | 0.38 | 0.53 | N | 0.63 | 0.5 |
| | | 0.31 | | 0.28 | | 0.56 | | | 0.53 |
| | | 0.25 | | 0.25 | | | | | 0.63 |
| Pa14 | Col$^R$ | 0.38 | N | N | N | 0.53 | 0.75 | 0.56 | 0.63 |
| | | | | | | 0.5 | 0.63 | 0.75 | 0.5 |
| | | | | | | 0.56 | | 0.5 | 0.75 |
| Pa058 | Col$^R$, Cip$^R$ Tob$^R$ | N | N | N | N | 0.75 | 0.53 | 0.52 | 0.56 |
| | | | | | | 0.53 | 0.56 | 0.56 | 0.5 |
| | | | | | | 0.56 | | 0.5 | 0.75 |
| | | | | | | 0.5 | | 0.53 | |
| | | | | | | | | 0.63 | |
| | | | | | | | | 0.75 | |
| Pa57388A | Col$^R$ | 0.38 | N | 0.31 | 0.38 | 0.52 | 0.63 | 0.63 | 0.5 |
| | | 0.31 | | 0.38 | | 0.51 | | 0.75 | 0.56 |
| | | | | | | 0.63 | | 0.5 | 0.75 |
| | | | | | | 0.56 | | 0.56 | |

TABLE 1-continued

| Strain | Antibiotic Resistance | Col | Cip | Tob | Gent | Col | Cip | Tob | Gent |
|---|---|---|---|---|---|---|---|---|---|
| Pa57388D | Col$^R$, Gent$^R$ | 0.31 0.38 | N | 0.38 0.31 0.25 | 0.38 | 0.62 0.53 0.56 0.5 | 0.53 0.56 0.52 0.75 | 0.56 0.51 0.52 | 0.5 0.63 0.51 |

| Cysteamine Hydrochloride (Cyst HCl) | | | | | | | | | |
|---|---|---|---|---|---|---|---|---|---|
| | Antibiotic | Cyst HCl FICI (Synergy) | | | | Cyst HCl FICI (Additive) | | | |
| Strain | Resistance | Col | Cip | Tob | Gent | Col | Cip | Tob | Gent |
| Pa01 | Col$^R$ | 0.125 0.14 0.28 0.26 | N | 0.25 0.31 0.38 0.28 0.19 | N | 0.5 0.5 | 0.75 0.52 0.56 | 0.51 0.53 0.5 | 0.75 0.5 |
| Pa14 | Col$^R$ | 0.125 0.28 0.19 0.09 | 0.31 0.37 0.38 | N | N | 0.51 0.5 0.53 0.52 | 0.56 0.63 0.5 | 0.63 0.75 0.5 | 0.5 0.63 0.56 |
| Pa058 | Col$^R$, Cip$^R$ Tob$^R$ | 0.38 | N | N/A | N | 0.52 0.75 0.56 0.5 | 0.53 0.63 0.75 0.56 | N/A | 0.75 |
| Pa57388A | Col$^R$ | 0.25 0.31 0.19 0.26 | 0.19 0.25 | N | N | 0.53 0.52 0.5 | 0.53 0.5 0.63 0.56 0.75 | 0.63 0.75 | 0.63 |
| Pa57388D | Col$^R$, Gent$^R$ | 0.19 0.28 0.25 0.31 | 0.31 0.38 | 0.25 0.31 0.19 | N | 0.52 0.53 | 0.56 0.53 | 0.51 0.5 | 0.53 0.52 |

| N-Acetyl Cysteine (NAC) | | | | | | | | | |
|---|---|---|---|---|---|---|---|---|---|
| | Antibiotic | NAC FICI (Synergy) | | | | NAC FICI (Additive) | | | |
| Strain | Resistance | Col | Cip | Tob | Gent | Col | Cip | Tob | Gent |
| Pa01 | Col$^R$ | N/A | N | N | N | N/A | 0.56 0.75 | 0.53 0.52 0.5 0.56 | N |
| Pa14 | Col$^R$ | N | N | N | N | 0.5 0.75 | 0.56 0.75 | 0.63 0.5 0.75 | 0.51 0.52 |
| Pa058 | Col$^R$ Cip$^R$ Tob$^R$ | N | N | N | N | 0.53 | 0.56 0.75 | 0.75 0.53 0.51 | 0.53 |
| Pa57388A | Col$^R$ | N | N | N | N | 0.56 0.75 0.52 | 0.63 0.5 0.56 | 0.53 | 0.63 |
| Pa57388D | Col$^R$ Gent$^R$ | N | N | 0.25 0.31 | N | 0.56 0.75 0.53 0.5 0.51 | 0.53 0.75 | 0.56 0.63 | N |

2.3

TABLE 2

Antimicrobial Efficacy of Cysteamine and Structurally Related Compounds versus Selected Clinically Relevant Isolates of *Pseudomonas aeruginosa*.

| | MIC (µg/ml) | | |
|---|---|---|---|
| Strain | MIC$_{50}$ | MIC$_{90}$ | MIC$_{100}$ |
| Cysteamine | | | |
| Pa01 | 250-500 | 500 | 666.67 |
| Pa14 | 125-250 | 500 | 1333.33 |
| Pa058 | 500 | 1000 | 1000 |
| NH57388A | 250 | 250-500 | 666.67 |
| Cystamine | | | |
| Pa01 | 250-1000 | 1000-2000 | 2000 |
| Pa14 | 125-250 | 1000-2000 | 2000 |
| Pa058 | 250-500 | 1000-2000 | 2000 |
| NH57388A | 500-1000 | 1000-2000 | 2000 |

TABLE 2-continued

Antimicrobial Efficacy of Cysteamine and Structurally Related Compounds versus Selected Clinically Relevant Isolates of *Pseudomonas aeruginosa*.

| Strain | MIC (μg/ml) | | |
|---|---|---|---|
| | $MIC_{50}$ | $MIC_{90}$ | $MIC_{100}$ |
| Taurine | | | |
| Pa01 | >2000 | >2000 | >2000 |
| Pa14 | >2000 | >2000 | >2000 |
| Pa058 | >2000 | >2000 | >2000 |
| NH57388A | >2000 | >2000 | >2000 |
| 2,3-Dimercaptosuccinic Acid | | | |
| Pa01 | 1000-2000 | >2000 | >2000 |
| Pa14 | 1000-2000 | 1000-2000 | >2000 |
| Pa058 | 500-2000 | 1000-2000 | 2000 |
| NH57388A | 500-2000 | 1000-2000 | 2000 |

In all cases, cysteamine demonstrated greater antimicrobial efficacy than the related compounds, indicating the essential nature of both the sulfhydryl and amine groups for significant antimicrobial activity.

Example 2

Figure 11:
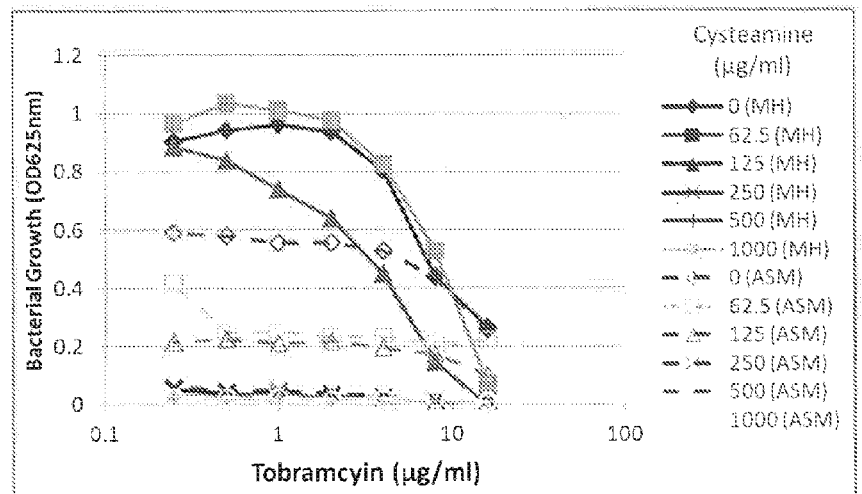
FIG. 11: shows a graph demonstrating the enhanced antimicrobial activity (reversal of resistance/insensitivity) of tobramycin against the Multidrug-Resistant *Burkholderia cepacia* NCTC10743 under CLSI Conditions (MH broth) and in Artificial Sputum Medium (ASM).
Figure 12:
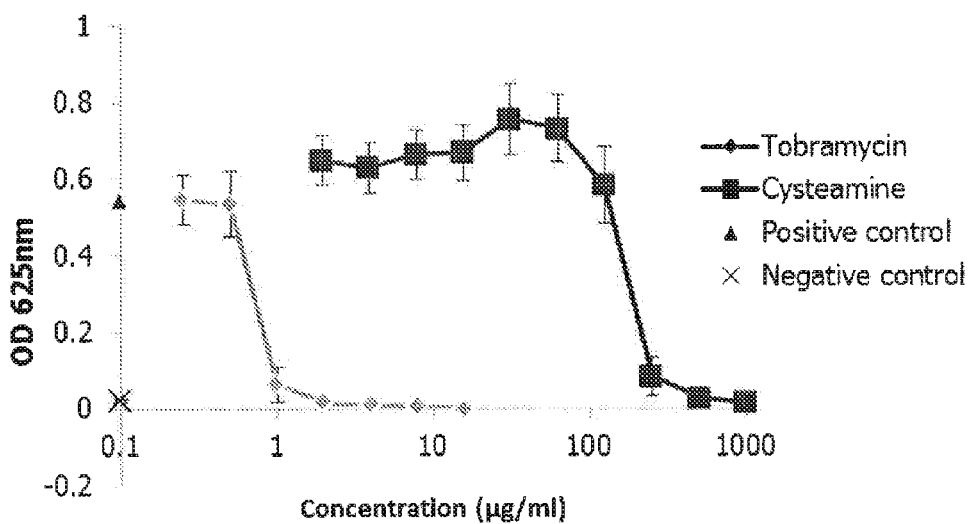
FIG. 12: shows a graph demonstrating the antimicrobial activity of tobramycin against *P. aeruginosa* and the antimicrobial activity of cysteamine against *P. aeruginosa* in standard CLSI conditions (MH broth).
Figure 13:
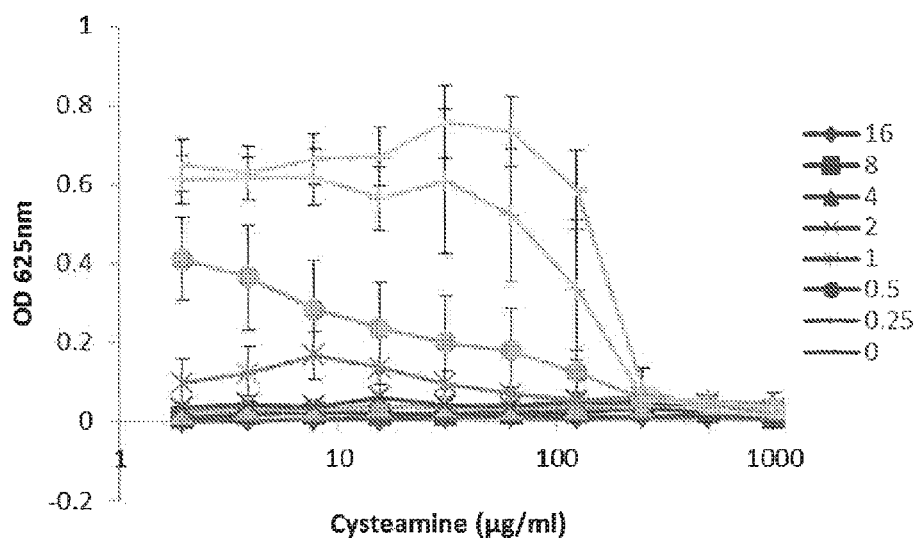
FIG. 13 shows a graph demonstrating the antimicrobial activity of tobramycin in combination with cysteamine against *P. aeruginosa* in standard CLSI conditions (MH broth).
Figure 14:
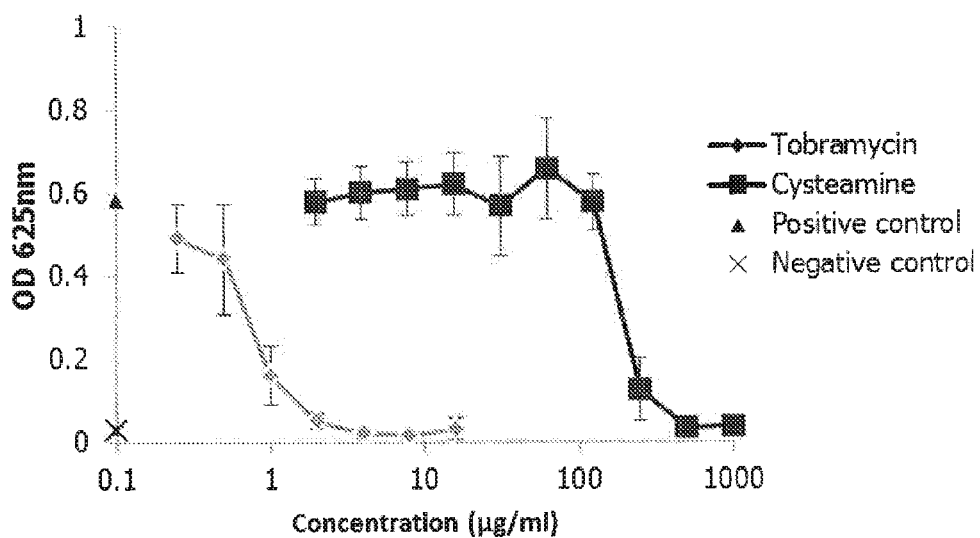
FIG. 14: shows a graph demonstrating the antimicrobial activity of tobramycin against *P. aeruginosa* and the antimicrobial activity of cysteamine against *P. aeruginosa* in Artificial Sputum Medium (ASM).
Figure 15:
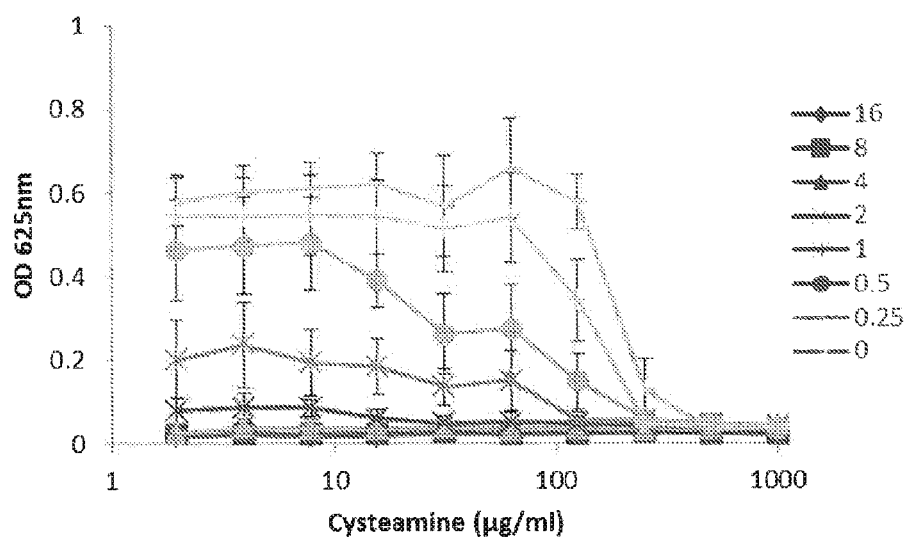
FIG. 15 shows a graph demonstrating the antimicrobial activity of tobramycin in combination with cysteamine against *P. aeruginosa* in Artificial Sputum Medium (ASM).
Figure 16:
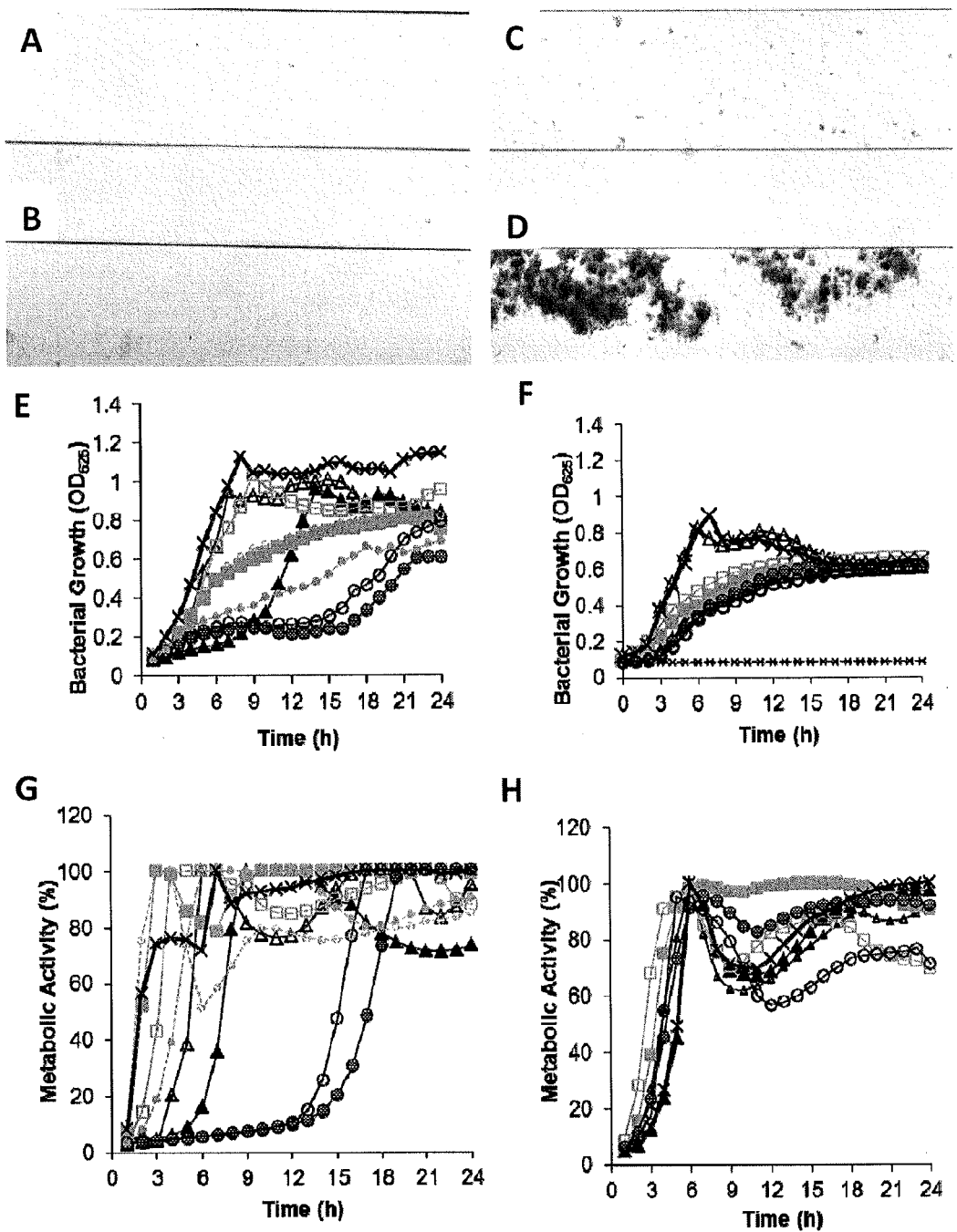
FIG. 16 shows microscopic images (A to D) of *P. aeruginosa* PAO1 Biofilms grown for 16 hours in BioFlux200 microfluidic channels and treated with a combination of:
A. Cysteamine-Tobramycin (500/50 µg/ml),
B. Cysteamine-Tobramycin (500/10 µg/ml),
C. N-acetylcysteine-Tobramycin (1000/50 µg/ml),
D. N-acetylcysteine-Tobramycin (1000/10 µg/ml),
and the post-antimicrobial effects of the combinations described above with relation to FIG. 16 by following bacterial growth (A and B), and metabolic activity (G and H) over a 24 hour period following treatment.

The complex pathophysiology of CF is characterized by airway obstruction caused by abnormal mucus secretion and infection, with 60-80% of patients being chronically infected with the biofilm-forming bacteria *Pseudomonas aeruginosa* (George et al., 2009). With a prevalence of up to 10% in adult CF patients, *B. cepacia* complex is a rare but major concern due to its high virulence, morbidity and transmissibility (O'Malley, 2009; Brüssow, 2012). We tested the antimicrobial activity of cysteamine-tobramycin combinations in artificial sputum medium (Yang, et al., 2011) against 4 *P. aeruginosa* (PAO1, ATCC27853, DSMZ1128 and DSMZ1299) and 2 *B. cepacia* complex strains (NCTC10743 and NCTC10744). For all strains, the $MIC_{100}$ of cysteamine ranged between 250 and 500 μg/ml in both CLSI condition (MH broth) and in artificial sputum medium and tobramycin activity was enhanced in the presence of cysteamine. The FIC index for the 4 *P. aeruginosa* strains was between 0.5 and 1 in both conditions, which indicates at least additive antimicrobial activity of these compounds in MH broth and artificial sputum medium (Charrier et al., in preparation). Table A summarises the data obtained against the *B. cepacia* strains, which are multidrug resistant microorganisms and intrinsically resistant to aminoglycosides, including tobramycin, and for which there are no CLSI interpretive criteria (Moore & Hancock, 1986; Hancock, 1998). FIG. 11 shows the result for *B. cepacia* NCTC10743. In both media, the $MIC_{100}$ of tobramycin was >16 μg/ml and the $MIC_{100}$ of cysteamine was 500 μg/ml. When combined, cysteamine made tobramycin efficacious and restored the susceptible phenotype; tobramycin $MIC_{100}$=0.25 ng/ml, in combination with 250 ng/ml cysteamine, which is 50% of the $MIC_{100}$ (FIC index <0.52, indicating at least additive antimicrobial activity and possibly synergy) (Burkhart et al., 2006).

This restoration of antibiotic sensitivity to *B. cepacia*, highlights the potential benefits of Lynovex® (cysteamine) for the treatment of the infections associated with cystic fibrosis. These results emphasise the potential for cysteamine to be used in combination therapy with other antibiotics including but limited to aminoglycoside and lipopeptide antibiotics in the treatment of CF.

TABLE A

Additive Antimicrobial Activity ($MIC_{100}$, μg/ml) of Lynovex ® (cysteamine) and the CF Antibiotic Tobramycin Against *Burkholderia cepacia*.

| | *B. cepacia* NH10743 | *B. cepacia* NH10744 |
|---|---|---|
| Lynovex ® (CLSI) | 250 | 250 |
| Tobramycin (CLSI) | >16 | >16 |
| Lynovex ®/Tobramycin (CLSI) | 125/16 | 250/0.25 |
| FIC index (CLSI) | <1.5 | <1.5 |
| Lynovex ® (ASM) | 500 | 500 |
| Tobramycin (ASM) | >16 | >16 |
| Lynovex ®/Tobramycin (ASM) | 125/16 | 250/0.25 |
| FIC index (ASM) | <0.52 | <0.52 |

CLSI: Clinical Laboratory and Standard Institute, approved standard M07-A9;
ASM: Artificial Sputum Medium (Yang et al., 2011);
FIC: Fractional Inhibitory Concentration (Burkhart et al., 2006).

The invention claimed is:

1. A method of treating an infection selected from the group consisting of a *Pseudomonas aeruginosa* infection and a *Burkholderia* spp infection by prophylaxis or therapy comprising the sequential or combined administration in a therapeutically effective amount of:
    an antibiotic agent selected from the group consisting of Tobramycin, Colistin, Gentamicin or Ciprofloxacin; and
    cysteamine, wherein the FIC index of the combination is less than 1.

2. A method as claimed in claim 1 wherein no peptide is present.

3. A method as claimed in claim 1 wherein the microbial infection is a topical infection or a systemic infection.

4. A method as claimed in claim 3 wherein the systemic infection is a mucosal infection.

5. A method as claimed in claim 4 wherein the mucosal infection is a gastrointestinal, urogenital or respiratory infection.

6. A method as claimed in claim 4 wherein the mucosal infection is associated with cystic fibrosis or is associated with chronic obstructive pulmonary disease (COPD).

7. A method as claimed in claim 3 wherein the infection is selected from the group consisting of skin and wound infections, middle-ear infections, gastrointestinal tract infections, peritoneal membrane infections, urogenital tract infections, oral soft tissue infections, formation of dental plaque, eye infections, endocarditis, infections in cystic fibrosis, and infections of indwelling medical devices.

8. A method as claimed in claim 7 wherein the infection is of a mucolytic environment.

9. A method as claimed in claim 8 wherein the infection is a bacterial infection associated with cystic fibrosis.

\* \* \* \* \*